(12) United States Patent
Silberstein et al.

(10) Patent No.: US 8,135,207 B2
(45) Date of Patent: Mar. 13, 2012

(54) OPTICAL INSPECTION TOOLS FEATURING PARALLEL POST-INSPECTION ANALYSIS

(75) Inventors: Shai Silberstein, Rishon-Le-Zion (IL); Tsafrir Avni, Shoam (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 928 days.

(21) Appl. No.: 12/145,701

(22) Filed: Jun. 25, 2008

(65) Prior Publication Data

US 2009/0324057 A1    Dec. 31, 2009

(51) Int. Cl.
*G06K 9/00* (2006.01)
*G01N 21/88* (2006.01)

(52) U.S. Cl. .............. 382/145; 382/149; 356/237.2; 356/237.5

(58) Field of Classification Search .......... 382/141, 382/145, 149
See application file for complete search history.

(56) References Cited

U.S. PATENT DOCUMENTS

| | | | |
|---|---|---|---|
| 5,699,447 A | 12/1997 | Alumot et al. | |
| 6,208,751 B1 * | 3/2001 | Almogy | 382/149 |
| 6,724,473 B2 | 4/2004 | Leong et al. | |
| 2004/0146295 A1 | 7/2004 | Furman et al. | |
| 2008/0037933 A1 | 2/2008 | Furman et al. | |

OTHER PUBLICATIONS

Shomroni et al. U.S. Appl. No. 11/764,296, filed Jun. 18, 2007, Optical Ispection Including Partial Scanning of Wafers.
Furman et al. U.S. Appl. No. 11/503,859, filed Aug. 14, 2006, Speckle Reduction Using a Fused Fiber Bundle and Light Guide.

* cited by examiner

*Primary Examiner* — F. L. Evans
(74) *Attorney, Agent, or Firm* — SNR Denton US LLP

(57) ABSTRACT

An optical inspection tool can automatically perform analysis/operations after the tool has generated data identifying defects (e.g. a defect list) from an inspection run of an object such as a semiconductor wafer. The tool can decouple post-inspection tasks from performing inspection runs so that one or more post-inspection tasks are performed on defect data from a previous inspection run while another inspection run is in progress. This can significantly improve the throughput of the tool when multiple inspections are performed, since the inspection run time effectively is shortened to include only the time the tool is actually used to acquire defect data. One or more post-inspection tasks can be performed, including, but not limited to, merging inspection runs, removing duplicate defects, removing straight-line false alarms, and characterizing defects.

19 Claims, 4 Drawing Sheets

Wafer I – Post Insp.

Wafer I - Inspection

Wafer II - Inspection

T

OPTICAL INSPECTION TOOLS FEATURING PARALLEL POST-INSPECTION ANALYSIS

BACKGROUND

Ongoing developments in semiconductor structures demand accurate inspection. In the field of inspection of semiconductor wafers and other objects (e.g. flat panels, reticles, and the like), good results have been obtained in systems that create one or more image(s) of an object being inspected and, based on the image data, attempt to identify defects in/on the object.

In such systems, it is often advantageous to perform additional analysis or operation on data identifying defects and/or suspected defects. Generally, these higher order analyses occur after initial analysis/operations that serve to identify defects/suspected defects, and can comprise more sophisticated analysis that can provide better inspection results.

For example, some systems may compare fields of view to identify defects. While this may be suitable for some applications, it may be advantageous to perform additional analysis of the identified defects, such as clustering, automatic defect classification (ADC), signature analysis, and the like, in order to provide more useful results.

SUMMARY

For purposes of this disclosure, the term "post-inspection task(s)" is used to refer to analysis/operations that occur after the tool has generated data identifying defects (e.g. a defect list) by performing an inspection run. An "inspection run" is an inspection of a full wafer, or part of a wafer as it is defined in the inspection recipe.

As set forth below, in some embodiments, an inspection system can be configured to decouple post-inspection tasks from performing inspection runs so as to perform one or more post-inspection tasks on defect data from a previous inspection run while another inspection run is in progress.

Post-inspection analysis can comprise a significant amount of time, depending on the type and number of tasks and the inspection data. By introducing the concept of task scheduling within operation of the inspection tool, some embodiments of the present subject matter can significantly improve the throughput of the tool when multiple inspections are performed, since the inspection run time effectively is shortened to include only the time the tool is actually used to acquire defect data. In addition, the throughput of the tool can become relatively steady as compared to a tool without parallel post-inspection; without parallel post-inspection, throughput can vary since the number of detected defects usually affects the run time of the post-inspection tasks.

For example, in some embodiments, a method of inspecting a semiconductor wafer can comprise performing a plurality of inspection of runs, each inspection run comprising steps of illuminating a wafer via one or more illumination sources, imaging at least a portion of the wafer, and analyzing the created image (or images) to produce data identifying a plurality of defects. Of course, it will be understood that the data may identify only "suspected defects," and post-inspection analysis may determine that some suspected defects are in fact not defects or are defects which are not a major concern.

In some embodiments, the inspection run can also include tasks such as loading a wafer onto a stage, performing alignment and other preliminary steps before imaging, and unloading the wafer after imaging.

The analysis of data identifying (suspected) defects is separated from the inspection run, though. Accordingly, the method can further comprise performing at least one post-inspection processing task on data identifying a plurality of defects from a previous inspection run while a different inspection run is in progress. The inspection runs may be inspections of different wafers or may be inspections of the same wafer.

The post-inspection processing task can comprise any number or type of operations on the defect data. For example, in some embodiments, a post-inspection processing task comprises attempting to determine if there are any duplicated defects in the data that identifies the defects. A "duplicated" defect as used herein is meant to refer to cases in which the data identifying defects accounts for the same defect multiple times.

In some embodiments, a post-inspection processing task comprises merging a plurality of inspection runs of the same object. For example, two or more inspection runs may be performed and defect data produced. The defect data from the two (or more) runs may be merged into a single defect file. Merging inspection runs may advantageously allow for better detection of certain defects, such as those that may be missed in a single inspection run.

In some embodiments, a post-inspection processing task comprises performing a defect signature analysis on one or more defects and/or performing automatic defect classification (ADC). For example, data identifying the defects can be used to assign a class for each defect. An example of signature analysis is finding a signature for all or some of the defects in an inspected area. Often, certain types of defects (such as defects tracable to certain types of production or process errors) will have a unique "fingerprint" that can be identified using signature analysis.

In certain embodiments, a post-inspection processing task comprises analyzing a listing of defects and removing indications of one or more defects reported to occur in a group positioned along a straight line. This is referred to as removal of straight-line false alarms. For instance, since wafers often have "Manhattan geometry," false alarms tend to be positioned along straight lines. Reducing such false alarms can increase the performance of an inspection tool.

As an example, removing a defect on a straight line in some embodiments comprises projecting defects from a plurality of dies into a defect list identifying each defect by its location in a single representative die. In the representative die, a plurality of narrow regions extending between any two opposite edges of the die can be identified. For example, the narrow regions may extend from the top to the bottom of the die with a narrow width, with other narrow regions extending between the sides of the die with a narrow height.

The method can comprise, for each narrow region, testing whether the number of defects in the narrow region exceeds a predetermined threshold. If the number of defects in the narrow region exceeds the predetermined threshold, some or all the defects in the narrow region can be deleted from the defect list.

In some embodiments, a semi-conductor inspection system can comprise at least one illumination source, an imaging system configured to create an image of at least a portion of an object at a focal plane, and a transporter configured to impart relative motion between the object and the focal plane so that the portion of the object that is in view of the focal plane can be varied. The system can further comprise at least one detector configured to receive light comprising the image of the object and provide data representing the image of the object and a control system. The control system can be configured to control the illumination source, transporter, and plurality of two-dimensional detectors during inspection runs and to analyze the data from the detector representing the image of the object and produce data identifying a plurality of defects. Further, the control system can be configured to perform at least one post-inspection processing task on data representing the identified defects from a previous inspection run at the same time that another inspection run is performed.

Another example of a post-inspection task is calculating a defect density. For example, some systems may provide statistical data, such as defect distributions or densities, by projecting defects into a single representative die or area. This analysis can be performed after an inspection run as a post-inspection task. Further, some inspection systems may image certain areas more than others during an inspection run. If defects from a plurality of imaged dies are projected into a single die for analysis, the post-inspection analysis can account for the fact that some defects are counted multiple times due to laying in an area that has been imaged multiple times.

It will be understood that the control system can vary in different embodiments. For example, the control system may comprise hardware and/or software. Further, the control system may comprise modules, such as a controller that handles operation of components during inspection runs (e.g. stage/illumination/detector timing, acquiring image data, identifying defects) and another controller or device that performs post-inspection tasks (e.g. analysis of identified defects). In some embodiments, the same controller can supervise the inspection runs and perform post-inspection tasks. The control system may be located physically or logically outside the tool, such as in a different system or part of another system interfaced with the tool. In any event, the control system can comprise any suitable arrangement of hardware and/or software, and it is not intended to limit the control system to any particular architecture.

BRIEF DESCRIPTION OF THE DRAWINGS

A full and enabling disclosure including the best mode of practicing the appended claims, directed to one of ordinary skill in the art, is set forth more particularly in the remainder of the specification, which makes reference to the appended figures, where like reference numerals are intended to represent analogous features, and in which:

Use of like reference numerals in different features is intended to illustrate like or analogous components.

DETAILED DESCRIPTION

Reference will now be made in detail to various embodiments of the present subject matter, one or more examples of which are illustrated in the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the disclosure herein includes modifications and variations as come within the scope of the appended claims and their equivalents.

The principles of operation discussed herein can be applied to any suitable inspection system. By way of example, a tool such as a Negevtech 3320, 3370, or other model inspection tool (available from Negevtech, Ltd. of Rehovot, Israel) can be suitably configured to implement one or more aspects of the present subject matter.

Figure 1:
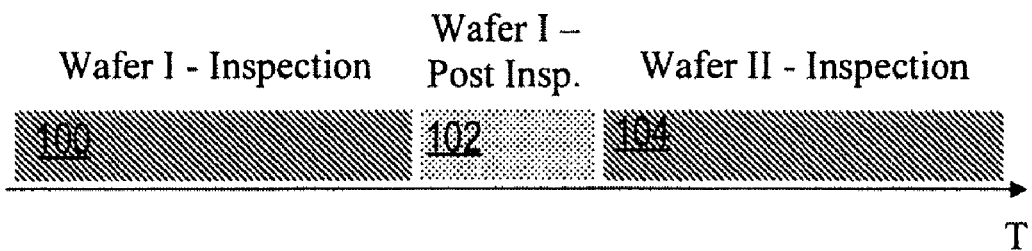
FIG. 1 is a timeline showing operation of an exemplary conventional tool.

FIG. 1 illustrates a timeline for operation of an exemplary conventional tool, with time increasing along the axis T. In this example, a first inspection (Wafer I-Inspection) is performed. This inspection has two time intervals: in time interval 100, data is acquired and (suspected) defects are identified, and in time interval 102, one or more analysis tasks are performed on the defect data. Time period 104 represents the beginning of another inspection (Wafer II-Inspection), in this example, an inspection of a second wafer, with the second inspection run followed by post-inspection tasks for that run.

Figure 2:
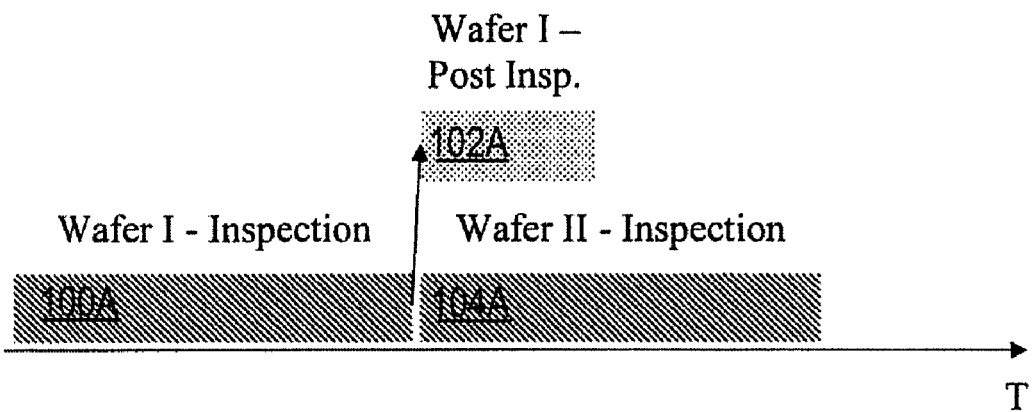
FIG. 2 is a timeline showing operation of an exemplary inspection tool configured in accordance with one or more aspects of the present subject matter.

FIG. 2 is a timeline for operation of an exemplary tool configured in accordance with the present subject matter, with time increasing along the axis T. Axis T is illustrated as having the same length as axis T of FIG. 1. Like FIG. 1, two inspection runs are illustrated. However, the same number of inspection runs are performed in less time in FIG. 2.

In this example, a first inspection run 100A is followed by a second inspection run 104A. In contrast to FIG. 1, in this timeline, post-inspection task(s) 102A are performed while the second inspection run 104A occurs. Thus, there is little or no delay between the first and second inspection runs since the post-inspection task(s) for inspection run 100A are decoupled from the actual run. Post-inspection task(s) for run 104A could be performed simultaneously with a third inspection run (not illustrated).

Any suitable post-inspection task or tasks may be performed. For instance, in some embodiments, straight-line false alarms can be removed. Although some tools, such as the Negevtech 3100 remove straight-line false alarms, such removal does not occur while another inspection run is in progress.

Figure 3:
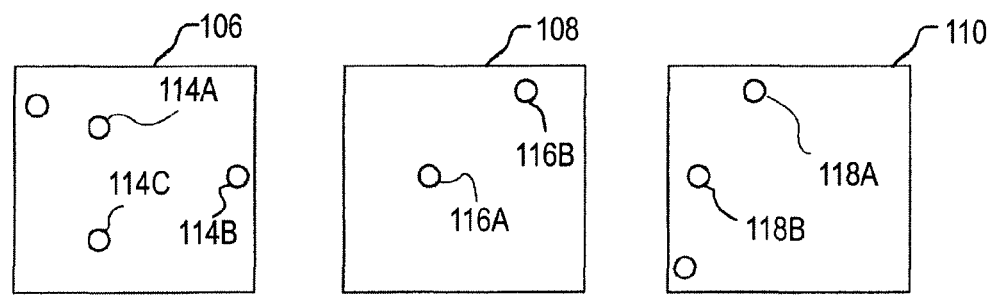
FIG. 3 is a diagram of exemplary dies combined into a single die.
Figure 3:
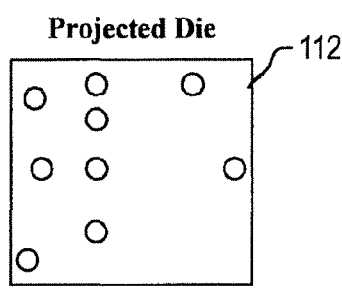

An example of the removal of straight-line false alarms will now be discussed in conjunction with FIGS. 3-4. FIG. 3 is a diagram illustrating three exemplary dies 106, 108, and 110, plus a "combined" or "projected die" 112. The tool has reported that each die has a plurality of respective defects, with exemplary defects 114A, 114B, and 114C shown on die 106; defects 116A and 116B shown on die 108; and defects 118A and 118B shown on die 110. In projected die 112, the defects from each die 106, 108, and 110 are superimposed onto a single die.

Figure 4:
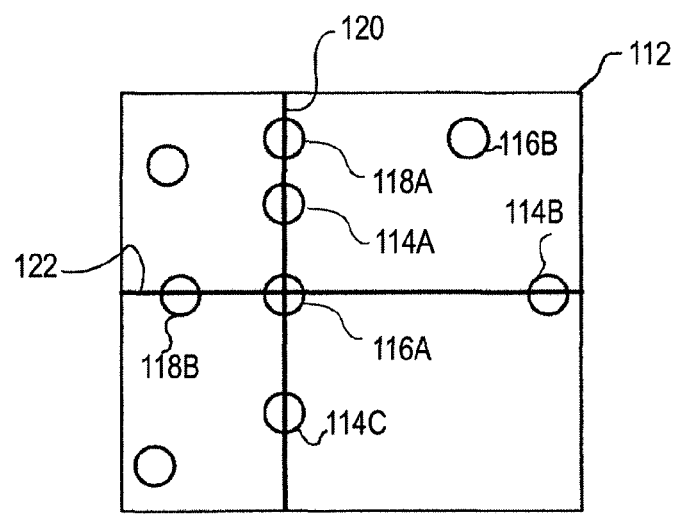
FIG. 4 is a close-up view of an exemplary merged die, along with an illustration of the removal of straight line false alarms.

As can be seen in FIG. 4, which is an exploded view of projected die 112, the defects from each die maintain their location relative to the die boundaries and to one another, but now all appear in the same die. This can allow for identification of patterns that might not be apparent otherwise if the dies were viewed in isolation.

For instance, geometry of a wafer, such as straight orthogonal lines (e.g. "Manhattan geometry") and patterned areas may lead to false alarms Oftentimes, the false alarms occur along horizontal and/or vertical straight lines. False alarms can be reduced by removing indications of defects where such indications meet certain criteria. For example, in some embodiments, straight-line false alarms are removed by first projecting defects reported by the tool into a single representative die, such as projected die 112. Then, a plurality of narrow regions extending between any two opposite edge of the die can be defined. For instance, in FIG. 4, two narrow regions 120 and 122 are shown. Narrow region 120 extends between the top and bottom edge of projected die 112 and has a narrow width, while narrow region 122 extends between the left and right edge of projected die 112 and has a narrow height.

In any event, for each narrow region, defects in the region can be identified. Then, a test can be performed to determine if the number of indicated defects in the narrow region exceed a predetermined threshold. The predetermined threshold may be a value provided by an operator, such as a recipe parameter. If the number of indicated defects in the narrow region exceed the predetermined threshold, the indications of the defects in the narrow region can be deleted from the defect list or flagged as possible straight-line false alarms.

Turning to the example of FIG. 4, it can be seen that four defects (118A, 114A, 116A, 114C) lie along narrow region 120, while three defects (118B, 116A, 114B) lie along narrow region 122. Other defects (e.g. 116B) do not appear to lie along the same line/narrow region extending between any two opposite edges of the die. Thus, if the threshold is, for example, two, then all defects (118A, 114A, 116A, 114C, 118B, 116A, 114B) may be removed or flagged. If the threshold is (greater than or equal to) four, then only defects (118A, 114A, 116A, 114C) may be flagged or removed.

In this example, the regions have a much smaller width relative to the defects. In practice, since the regions have a constant width without any consideration of the defect size, the relative size of the regions to defects will vary, since defects of many different sizes can be obtained in a single inspection. Further, the narrow regions may effectively comprise lines, rather than rectangles. In practice, the narrow regions may be discrete, or may overlap.

Additionally, many more evaluations will typically occur than in the simplified example above. For example, a plurality of vertical regions may be defined extending between the top and bottom, and a plurality of horizontal regions may be defined extending between the left and right sides, of die 112. The end result in some embodiments is that each part of the die has been covered as part of at least two orthogonal regions, with the number of defects falling within each region checked against the threshold.

Although this example discussed horizontal and vertical regions, in other embodiments, diagonal lines of any suitable angle could be used. For example, a plurality of lines at 45 degrees relative to the die edges could be used for analysis.

Other post-inspection tasks may be performed. For instance, clustering may be performed to identify one or more clusters of defects based on defect data. For instance, any kind of distance measurement, including, but not limited to, the Euclidean distance between the center of gravity of the defects may be used.

In some embodiments, clusters are defined as groups of one or more connected defects. For instance, each defect that is connected to one (or more) defects in the cluster can be considered part of the cluster. A pair of defects can be considered to be connected if the distance between the defects is less than a threshold value determined by the following equation, where $C_1$, $C_2$, and $C_3$ are user-specified constants:

$$\mathrm{Max}\left[C_1 \cdot \left(\sqrt{\mathrm{Size}(\mathit{Defect}_1)} + \sqrt{\mathrm{Size}(\mathit{Defect}_2)}\right) + C_2, C_3\right]$$

Properties of a cluster can be determined based on the defects comprising the cluster. For example, the cluster size can be determined by summing the sizes from the defects in the cluster; the cluster energy can be the sum of the energies from all defects in the cluster; the center of gravity of the cluster can be determined from the center of gravity of all defects in the cluster. Cluster boundaries can be determined, such as a bounding rectangle that bounds all the defects in the cluster.

It should be understood that other criteria can be used to define clusters other than connectivity, and even when connectivity is used, other criteria can be used to determine if defects are connected. For example, the distance between defects may be compared to a constant, rather than using the equation noted above to determine the threshold value.

Another example of a post-inspection task is removal of "duplicate" defects. When a wafer is scanned, one or more portions of the wafer may be inspected multiple times. For example, if the wafer is inspected via a plurality of images, some of the images may overlap. A defect may be identified more than one time from the multiply-inspected areas. A "duplicated" defect as used herein is meant to refer to cases in which the data identifying defects accounts for the same defect multiple times.

In some embodiments, duplicate defects can be removed by applying a variant of clustering. Namely, the defects can be clustered using a very small clustering distance. Then, in each cluster, the largest defect is selected, while the other defects are deleted from the data or flagged as likely duplicates.

Another example of a post-inspection task is merging two inspection runs of the same wafer. Defects identified in two or more runs can be combined in order to identify more defects, in order to reduce false alarms, and/or in order to obtain more data about each defect. For example, certain defects may not always be detected in any given inspection run, but the likelihood of detection may rise if multiple runs are performed. As another example, defects may appear different in different inspection modes.

In any event, after the last of a group of inspection runs of interest, a defect merging task can be carried out. This post-inspection task may occur while another inspection run is performed (e.g. an inspection run for another wafer).

Next, an example of merging two inspection runs will be discussed. Initially, for each defect of the first inspection run, the tool checks to see if there is a matching defect identified in the second inspection run. Matching defects may be identified by determining if two defects are close enough to one another, such as by measuring their distance. After matching defects are identified, a merged list can be created in any number of ways.

For example, in some embodiments, the merged list is created by a "Union" between the runs—that is, the merged list comprises all defects from the two inspection runs, but the matched defects are only included in the list once.

In some embodiments, the merged list is created by an "Intersection" between the runs—that is, only defects found in both inspection runs are considered. Again, matched defects are only included once.

The merged list may be created by an "Only First" or "Only Second" operation between the runs. In one embodiment, only defects found in the first inspection run, but not in the second inspection run are included in the merged list. In another embodiment, only defects found in the second inspection run, but not in the first are included in the merged list.

Generally, when two defects are matched and only one is included in the merged list, the larger defect remains in the list. However, in some embodiments, defect data from both runs is retained for further analysis if required. For instance, when a merged list is assembled, defects not included in the merged list may be flagged, but not deleted. Alternatively, the defects in a set of data that are in the merged list may be flagged to identify them from the other defects not in the merged list.

Although the examples above related to merging two inspection runs, it will be understood that the same principles may apply when merging more than two inspection runs. The manner in which the runs are merged can vary according to the number of runs and the type of operation.

Another example of a post-inspection task is calculating a defect density. For example, some systems may provide statistical data, such as defect distributions or densities. The density may represent the number of defects per square millimeter (or other unit) across a die, wafer, or area. This type of analysis can be performed after an inspection run as a post-inspection task. Namely, defects from a plurality of dies can be projected into a single representative die. Then, defects per square millimeter (or other unit) can be counted.

Some inspection systems may image certain areas more than others during an inspection run. If defects from a plurality of imaged dies are projected into a single die for analysis, the post-inspection analysis can account for the fact that some defects are counted multiple times due to laying in an area that has been imaged multiple times. See, for example, U.S. patent application Ser. No. 11/764,296, entitled OPTICAL INSEPCTION INCLUDING PARTIAL SCANNING OF WAFERS, filed Jun. 18, 2007 and assigned to Negevtech, Ltd. application Ser. No. 11/764,296 is incorporated by reference herein in its entirety to the extent it is not in conflict with the present subject matter.

Figure 5:
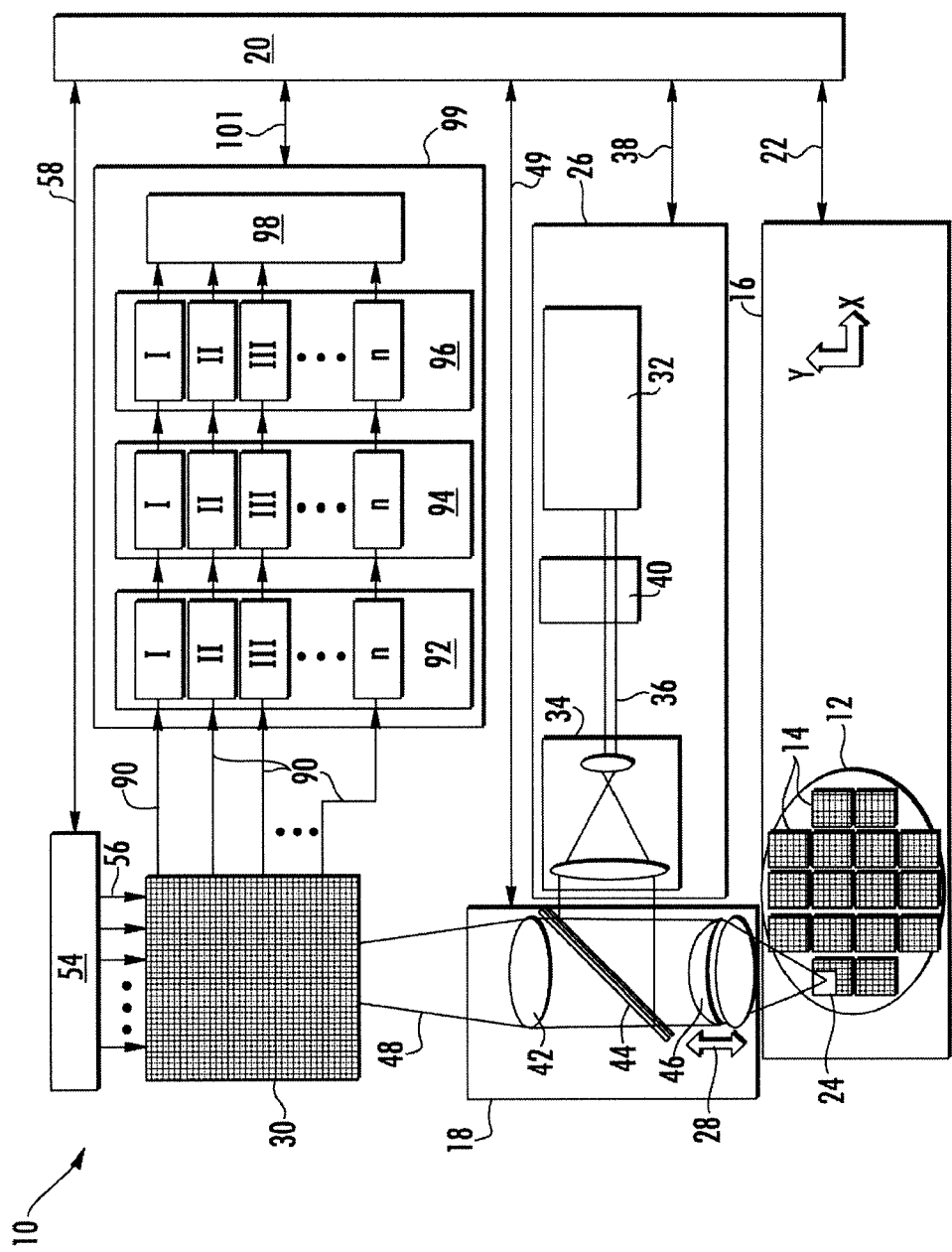
FIG. 5 is a block diagram showing illumination, imaging, and control components in an exemplary optical inspection tool.
Figure 6:
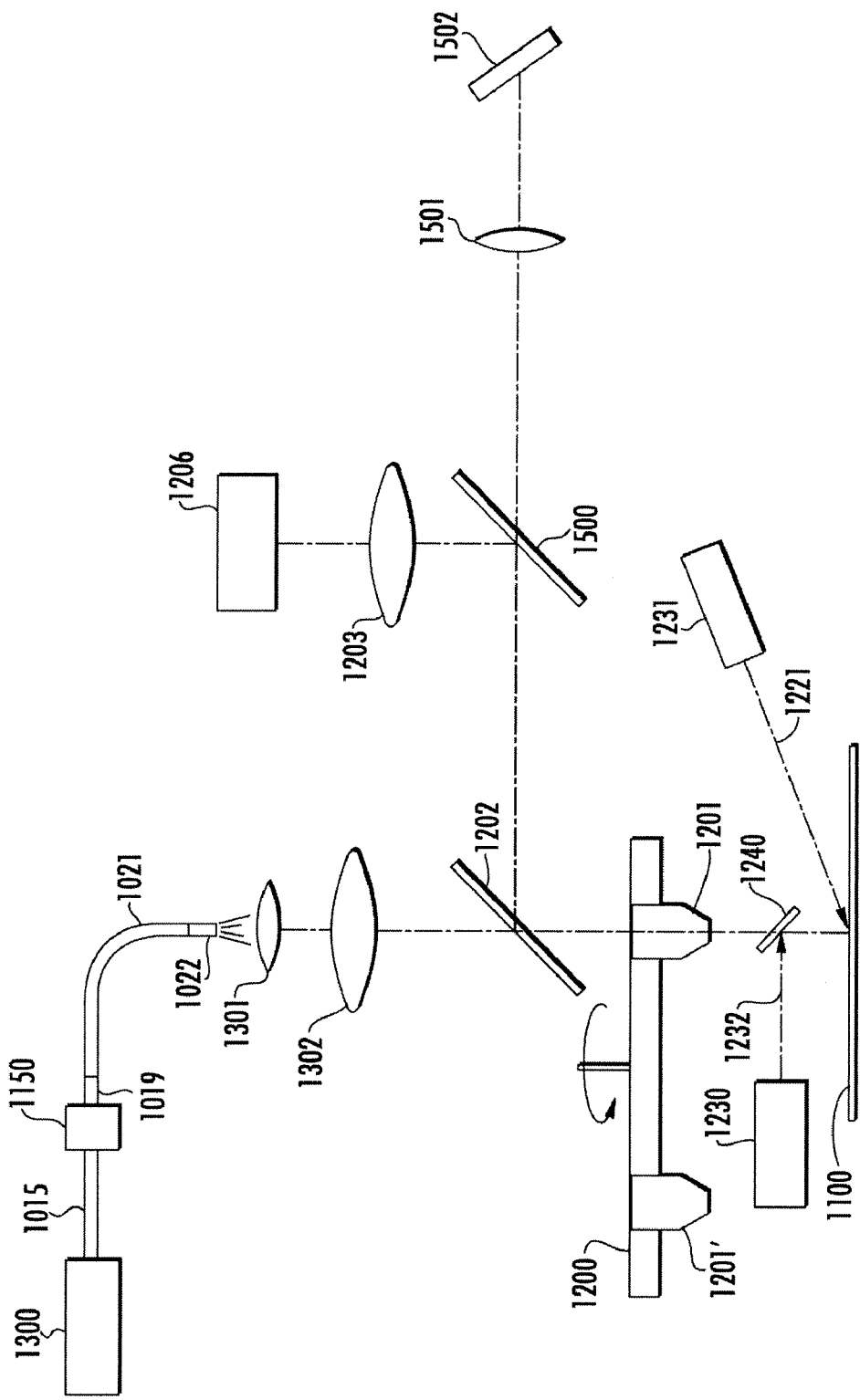
FIG. 6 is a block diagram showing additional aspects of imaging and illumination in an exemplary optical inspection tool.

FIGS. 5 and 6 depict aspects of an exemplary electro-optical inspection system. In this example, FIG. 5 is a schematic diagram illustrating an exemplary embodiment of a system for fast on-line electro-optical detection of wafer defects, while FIG. 6 shows a schematic illustration of an object inspection system utilizing a laser source and a fiber optical delivery bundle in an exemplary inspection tool. For instance, the tool may comprise a Negevtech 3320, 3370, or other model optical inspection tool (available from Negevtech, Ltd. of Rehovot, Israel), modified to implement one or more aspects of the post-inspection subject matter discussed herein. Additional details regarding exemplary aspects of an optical inspection system can be found in U.S. patent application Ser. No. 10/345,097, published as US20040146295 A1 on 29 Jul. 2004, which is incorporated by reference herein for all purposes to the extent it is not in conflict with the present subject matter.

It is to be noted that the operating principles discussed below can be used in any suitable inspection system.

As shown in FIG. 5, an inspection tool can include a focal plane assembly 30 comprising pixels from multiple two-dimensional detectors. Focal plane assembly 30 is configured so that a continuous surface of photodetectors is optically formed at the focal plane of imaging optics 18. The actual photodetectors can be located at different geometric locations. The inspection image obtained at the focal plane of imaging optics 18 can be split in any suitable fashion.

In operation, the dies 14 of wafer 12 can be illuminated in any suitable manner, such as by laser light from pulsed illumination system 26. Light 48 represents rays of light scattered, reflected, and diffracted by the wafer. This light can be collected using imaging optics 18. In this example, imaging optics 18 comprise a beam splitter 44 (used in illuminating wafer 12 with light from laser system 26), focusing lens 42, and an objective lens 46 which may be adjusted using an auto-focus system 28 (not shown in detail). In this example, focusing lens 42 focuses light 48 onto focal plane assembly 30 and defines the focal plane of imaging optics 18. However, the actual content and arrangement of a particular set of imaging optics can vary.

A patterned semiconductor wafer 12 featuring a plurality of wafer dies 14, is placed and aligned on a continuous moving XY translation stage 16 to impart motion between the wafer and the components used to image the wafer. XY translation stage 16 moves wafer 12 typically in a serpentine pattern beneath an optical imaging system 18, thereby changing which area of the wafer is in view of the imager. However, movement patterns other than a serpentine pattern could be used. Additionally, the wafer may be moved in a different manner in other embodiments. Furthermore, in some embodiments, the wafer may remain stationary, with apparent motion between the wafer and component(s) used to image the wafer imparted by the use of one or more optical components. For instance, a rotating mirror can be used to move the field of view of imaging optics 18 in a serpentine (or other) pattern across the wafer. In other embodiments, relative motion may be imparted by moving both the wafer and adjusting optical components.

Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution. Control system 20 can comprise any suitable type or arrangement of components used to orchestrate the inspection process, including, for example, a microprocessor-based controller, a general-purpose or specialized computer system, and the like.

In this example, illumination system 26 includes a repetitively pulsed laser 32, a laser beam expander 34, a laser beam light path 36, control/data links 38, and a crystal 40 having non linear optical properties and serving as a 'second harmonic' or 'third harmonic' generating crystal. This type of illumination system enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38. Of course, the present subject matter can be used in any inspection system regardless of the particular type, mode, or manner of illumination.

Briefly, FIG. 6 illustrates exemplary components associated with illuminating an object in an inspection system. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination may be preferred. In order to detect a small particle on a surface, DF illumination can generally yield better results.

In bright field illumination in general, the illumination is incident on the sample through the same objective lens as is used for viewing the sample. FIG. 6 shows a bright field illuminating laser source 1300 delivering its output beam 1015 into an optical delivery fiber bundle 1021, preferably by means of a laser to fiber coupler 1150. This optical fiber bundle 1021 provides both uniform illumination on the sample and coherence breaking of the laser illumination. In some embodiments, only a single fiber bundle is used, but it is to be understood that a serially-arranged fiber bundle solution may also be suitable. In other embodiments, one or more bundles may be combined with further components, such as a light guide or guides. Discussion of exemplary fiber/light guide combinations can be found in co-pending U.S. Patent Application entitled "Speckle Reduction Using a Fiber Bundle and Light Guide," Ser. No. 11/503,859, filed Aug. 14, 2006, published as US20080037933A1 on Feb. 14, 2008, which is incorporated by reference herein for all purposes in its entirety to the extent it is not in conflict with the present subject matter.

From the output termination of the fiber bundle 1021, the laser beam is imaged by means of illumination transfer lenses 1301, 1302 onto the objective lens in use 1201, which is operative to focus the illumination onto a wafer 1100 being inspected. Appropriate alternative objective lenses 1201' can be swung into place on an objective revolver 1200, as is known in the microscope arts. The illumination returned from the wafer is collected by the same objective lens 1201, and is deflected from the illumination path by means of a beam splitter 1202, towards a second beam splitter 1500, from where it is reflected through the imaging lens 1203, which images the light from the wafer onto the detectors of the imager, with one of the detectors represented in FIG. 6 at 1206. In this example, only a single detector and optical path is shown for purposes of example. In practice, the path of light comprising the inspection image can, of course, vary. In this example, the second beam splitter 1500 is used to separate the light going to the imaging functionality from the light used in the auto-focus functionality, which is directed by means of the auto-focus imaging lens 1501 to the auto-focus detector 1502.

When dark field illumination is required for the imaging at hand, a dark field side illumination source 1231 is used to project the required illumination beam 1221 onto the wafer 1100. When orthogonal dark field, or obscured reflectance dark field illumination is required for the imaging at hand, an alternative dark field illumination source 1230 is used to project the required illumination beam 1232 via the obscured reflectance mirror 1240 onto the wafer 1100 orthogonally from above. FIG. 6 indicates sources 1300, 1231, and 1230 at different locations. However, any or all of sources 1300, 1230, and 1231 may comprise the same light source, with the bright field, dark field, and obscured reflectance dark field effects achieved through moving the source(s) and/or redirecting illumination to the appropriate angle using one or more optical components. Further, it is to be understood that other arrangements for laser illumination and/or other illumination methods entirely could be used in conjunction with the present subject matter.

In operation, one or more images of the wafer are obtained and the images are analyzed to determine the presence or absence of a defect or potential defect in the wafer. For example, the tool may include an image analysis system comprising one or more computers or other suitable image processing hardware configured to evaluate the images. In the example of FIG. 5, an image processing system 99 includes parallel configured image processing channels 90 for image grabbing by an image grabber 92, an image buffer 94, a defect detection unit 96, a defect file 98, and control/data links 101. Image data acquired by focal plane assembly 30 featuring twenty-four two-dimensional CCD matrix photo-detectors is processed in parallel, whereby each of the twenty-four CCD matrix photo-detectors communicates separately, in parallel to the other CCD matrix photo-detectors of focal plane assembly 30, with image grabber 92, via twenty-four separate image processing channels 90. Instead of processing image data using a single serial channel of 48 megapixels at a CCD frame speed acquisition rate of 60 times per second, resulting in a single channel with a very high, 3 gigapixels per second processing rate, each of the twenty-four or more separate image processing channels 90 having about 2 megapixels of image data, acquired at a rate of 60 times per second, is used for processing at a moderate rate of tens of megapixels per second. Image processing system 99 is in communication with central control system 20 via control/data links 101.

As another example, the tool may be connected to suitable hardware, or image data may be provided to suitable hardware in any other manner for later analysis.

Any suitable type(s) of analysis may be used to determine the presence or absence of defects. For example, the tool may obtain images on a frame-by-frame basis and compare single frames or groups of frames to references. As another example, the tool may analyze images without comparison to other images, such as locating bright spots on a dark area and/or dark spots on a light area. Any suitable comparison/analysis technique(s) may be used, including cell-to-cell comparison, die-to-die comparison, and may be carried out using any suitable software algorithm(s) and/or specialized hardware to analyze and process the images.

The above discussion is for purposes of example only with regard to illumination and imaging techniques. The present subject matter can be utilized in or in conjunction with any suitable inspection tool capable data of identifying a plurality of defects (or suspected defects).

In the example above, one or more analysis techniques applied by defect detection unit 96 result in data comprising the defect file 98. Data included in defect file 98 can be the subject of one or more post-inspection tasks. In some examples discussed above, the term "defect list" was used. Although the term "list" is used, a "defect list" may comprise any suitable form or collection of data that indicates suspected defects found by the inspection tool The post-inspection tasks may, for example, be performed using controller 20 and/or another suitable control system, such as a processor in communication with the tool that can access defect data and provide suitable output.

The detectors can comprise any suitable number, type, or combination of light-sensing elements. The underlying sensing can be based on any suitable technology. For instance, in various embodiments, one or more of the following types of detector types can be used: CCD, CMOS, PMT, and/or avalanche photodiode detectors.

The detectors may be of any suitable type. For example, one or more detectors may comprise an area detector, such as a matrix of photo-sensors producing 2 dimensional image data. As another example, one or more detectors can comprise a TDI line detector, i.e. a matrix of photo-sensors which produces 1 dimensional image data over time. As another example, one or more detectors can comprise a line detector i.e. a line of photo-sensors which produces 1 dimensional line image. In certain embodiments, a detector can comprise a "point detector," where each detector signal represents a pixel.

It will be appreciated that, in some embodiments in which light sensing and imaging is based on point detection, such as when PMT and/or avalanche photodiode detectors are used, the illumination and/or imaging hardware will need to be varied appropriately from the example arrangements discussed above in conjunction with FIGS. 5 and 6. For example, embodiments of a tool using PMT and/or avalanche photodiode detectors can include some sort of scanning mechanism to variably illuminate spots on the wafer or other object(s) under inspection. For instance, a suitable illumination source (such as an argon laser or another laser) can be used in conjunction with an acousto-optical deflector to scan one or more illuminating beams across the wafer or other object(s) under inspection.

As one example of inspecting using a scanning source, a sawtooth pattern in the time domain can be used while the stage moves the wafer orthogonally to the movement of the illuminating beam. The imaging optics can be arranged to appropriately collect light from the illuminating beam as reflected or otherwise scattered by the wafer. Exemplary details of an inspection system including a scanning illumination source can be found in U.S. Pat. No. 5,699,447, which is incorporated by reference herein in its entirety to the extent it does not conflict with the present subject matter. Exemplary discussion of line detection can be found in U.S. Pat. No. 6,724,473, which is incorporated by reference herein in its entirety to the extent it does not conflict with the present subject matter.

When TDI or line detection is used, illumination and relative movement of the wafer should be adjusted accordingly, with the image acquisition hardware/software also suitably configured. For instance, as is known in the art, when TDI detection is used, continuous illumination is applied while the imaging location on the wafer or other object is varied.

Similarly, the hardware/software used for image acquisition/analysis should be appropriately configured for embodiments in which point detection is used. Namely, rather than capturing an entire field of view instantaneously, the imaging hardware images a series of points (which may each comprise one or more pixels) or lines from which the entire image of the wafer can be constructed.

The use of headings, letters, numbers, or other listing criteria in this document is not meant as a limitation, but is only intended as an aid to the reader.

It is appreciated by persons skilled in the art that the presently disclosed subject matter is not limited in scope by what has been particularly shown and described above, which constitute various examples. As set forth in the attached claims, the scope includes both combinations and sub-combinations of various features discussed herein, along with such variations and modifications as would occur to a person of skill in the art.

What is claimed:

1. A method, comprising:
    (a) performing a plurality of inspection runs to inspect semiconductor wafers, each of the inspection runs comprising:
        (i) illuminating one of the wafers via at least one illumination source,
        (ii) forming an image of at least a portion of the illuminated wafer, and
        (iii) analyzing the image to produce data identifying a plurality of defects; and
    (b) during at least one of the inspection runs, performing at least one post-inspection processing task on a portion of the data, the portion produced during an inspection run performed prior to the at least one of the inspection runs, wherein the at least one post-inspection processing task comprises attempting to identify duplicated defects from the data and removing identified duplicated defects from the data.

2. The method set forth in claim 1, wherein the at least one post-inspection processing task further comprises performing an automatic defect classification operation on at least one of the defects identified in the data.

3. The method set forth in claim 1, wherein during a first of the inspection runs, a first one of the wafers is inspected, and during a second of the inspection runs, a second one of the wafers different from the first wafer is inspected.

4. A method, comprising:
    (a) performing a plurality of inspection runs to inspect semiconductor wafers, each of the inspection runs comprising:
        (i) illuminating one of the wafers via at least one illumination source,
        (ii) forming an image of at least a portion of the illuminated wafer, and
        (iii) analyzing the image to produce data identifying a plurality of defects; and
    (b) during at least one of the inspection runs, performing at least one post-inspection processing task on a portion of the data, the portion produced during an inspection run performed prior to the at least one of the inspection runs, wherein the at least one post-inspection processing task comprises merging a plurality of inspection runs corresponding to one of the wafers.

5. The method set forth in claim 4, wherein two of the inspection runs corresponding to one of the wafers are merged.

6. A method, comprising:
    (a) performing a plurality of inspection runs to inspect semiconductor wafers, each of the inspection runs comprising:
        (i) illuminating one of the wafers via at least one illumination source,
        (ii) forming an image of at least a portion of the illuminated wafer, and
        (iii) analyzing the image to produce data identifying a plurality of defects; and
    (b) during at least one of the inspection runs, performing at least one post-inspection processing task on a portion of the data, the portion produced during an inspection run performed prior to the at least one of the inspection runs, wherein the at least one post-inspection processing task comprises attempting to identify at least one cluster of defects from the data.

7. A method, comprising:
    (a) performing a plurality of inspection runs to inspect semiconductor wafers, each of the inspection runs comprising:
        (i) illuminating one of the wafers via at least one illumination source,
        (ii) forming an image of at least a portion of the illuminated wafer, and
        (iii) analyzing the image to produce data identifying a plurality of defects; and
    (b) during at least one of the inspection runs, performing at least one post-inspection processing task on a portion of the data, the portion produced during an inspection run performed prior to the at least one of the inspection runs, wherein the at least one post-inspection processing task comprises performing a defect signature analysis on at least one of the defects identified in the data.

8. A method, comprising:
(a) performing a plurality of inspection runs to inspect semiconductor wafers, each of the inspection runs comprising:
   (i) illuminating one of the wafers via at least one illumination source,
   (ii) forming an image of at least a portion of the illuminated wafer, and
   (iii) analyzing the image to produce data identifying a plurality of defects; and
(b) during at least one of the inspection runs, performing at least one post-inspection processing task on a portion of the data, the portion produced during an inspection run performed prior to the at least one of the inspection runs, wherein the at least one post-inspection processing task comprises removing an indication of a straight-line false alarm.

9. The method set forth in claim 8, wherein removing an indication of a straight-line false alarm comprises:
projecting indicated defects from a plurality of dies into a defect list identifying each of the indicated defects by its location in a single representative die;
in the representative die, identifying a plurality of narrow regions extending between any two opposite edges of the representative die; and
for each of the narrow regions, testing whether a number of indicated defects in the narrow region exceeds a predetermined threshold, and if so, deleting all indications of defects in the narrow region from the defect list.

10. A method, comprising:
(a) performing a plurality of inspection runs to inspect semiconductor wafers, each of the inspection runs comprising:
   (i) illuminating one of the wafers via at least one illumination source,
   (ii) forming an image of at least a portion of the illuminated wafer, and
   (iii) analyzing the image to produce data identifying a plurality of defects; and
(b) during at least one of the inspection runs, performing at least one post-inspection processing task on a portion of the data, the portion produced during an inspection run performed prior to the at least one of the inspection runs, wherein the at least one post-inspection processing task comprises calculating a defect density for a plurality of areas on one of the wafers.

11. A system, comprising:
at least one illumination source;
an imaging system configured to form an image of at least a portion of an object at a focal plane;
a transporter configured to impart relative motion between the object and the focal plane so that the portion of the object that is in view of the focal plane can be varied;
at least one detector configured to receive light comprising the image of the object and provide data representing the image of the object; and
a control system configured to:
   (i) control the illumination source, the transporter, and the at least one detector during a plurality of inspection runs,
   (ii) analyze the data from the at least one detector representing the image of the object and produce data identifying a plurality of defects, and
   (iii) during at least one of the inspection runs, perform at least one post-inspection processing task on a portion of the data identifying the defects, the portion produced during an inspection run performed prior to the at least one of the inspection runs, wherein the at least one post-inspection processing task comprises attempting to identify duplicated defects from the data identifying the defects and remove said duplicated defects from the data identifying the defects.

12. The system set forth in claim 11, wherein the at least one post-inspection processing task comprises performing an automatic defect classification operation on at least one of the identified defects.

13. A system, comprising:
at least one illumination source;
an imaging system configured to form an image of at least a portion of an object at a focal plane;
a transporter configured to impart relative motion between the object and the focal plane so that the portion of the object that is in view of the focal plane can be varied;
at least one detector configured to receive light comprising the image of the object and provide data representing the image of the object; and
a control system configured to:
   (i) control the illumination source, the transporter, and the at least one detector during a plurality of inspection runs,
   (ii) analyze the data from the at least one detector representing the image of the object and produce data identifying a plurality of defects, and
   (iii) during at least one of the inspection runs, perform at least one post-inspection processing task on a portion of the data identifying the defects, the portion produced during an inspection run performed prior to the at least one of the inspection runs, wherein the at least one post-inspection processing task comprises merging a plurality of inspection runs of corresponding the object.

14. The inspection system set forth in claim 13, wherein two of the inspection runs corresponding to the object are merged.

15. A system, comprising:
at least one illumination source;
an imaging system configured to form an image of at least a portion of an object at a focal plane;
a transporter configured to impart relative motion between the object and the focal plane so that the portion of the object that is in view of the focal plane can be varied;
at least one detector configured to receive light comprising the image of the object and provide data representing the image of the object and a control system configured to:
   (i) control the illumination source, the transporter, and the at least one detector during a plurality of inspection runs,
   (ii) analyze the data from the at least one detector representing the image of the object and produce data identifying a plurality of defects, and
   (iii) during at least one of the inspection runs, perform at least one post-inspection processing task on a portion of the data identifying the defects, the portion produced during gin an inspection run performed prior to the at least one of the inspection runs, wherein the at least one post-inspection processing task comprises attempting to identify at least one cluster of defects within the identified defects.

16. A system, comprising:
at least one illumination source;
an imaging system configured to form an image of at least a portion of an object at a focal plane;
a transporter configured to impart relative motion between the object and the focal plane so that the portion of the object that is in view of the focal plane can be varied;
at least one detector configured to receive light comprising the image of the object and provide data representing the image of the object and a control system configured to:
  (i) control the illumination source, the transporter, and the at least one detector during a plurality of inspection runs,
  (ii) analyze the data from the at least one detector representing the image of the object and produce data identifying a plurality of defects, and
  (iii) during at least one of the inspection runs, perform at least one post-inspection processing task on a portion of the data identifying the defects, the portion produced during an inspection run performed prior to the at least one of the inspection runs, wherein the at least one post-inspection processing task comprises performing a defect signature analysis on at least one of the identified defects.

17. A system, comprising:
at least one illumination source;
an imaging system configured to form an image of at least a portion of an object at a focal plane;
a transporter configured to impart relative motion between the object and the focal plane so that the portion of the object that is in view of the focal plane can be varied;
at least one detector configured to receive light comprising the image of the object and provide data representing the image of the object; and
a control system configured to:
  (i) control the illumination source, the transporter, and the at least one detector during a plurality of inspection runs,
  (ii) analyze the data from the at least one detector representing the image of the object and produce data identifying a plurality of defects, and
  (iii) during at least one of the inspection runs, perform at least one post-inspection processing task on a portion of the data identifying the defects, the portion produced during an inspection run performed prior to the at least one of the inspection runs, wherein the at least one post-inspection processing task comprises removing a straight-line false alarm.

18. The system set forth in claim 17, wherein removing a straight-line false alarm comprises:
projecting indicated defects from a plurality of dies into a defect list identifying each of the indicated defects by its location in a single representative die;
in the representative die, identifying a plurality of narrow regions extending between any two opposite edges of the representative die; and
for each of the narrow regions, testing whether the a number of indicated defects in the narrow region exceeds a predetermined threshold, and if so, deleting all indications of defects in the narrow region from the defect list.

19. A system, comprising:
at least one illumination source;
an imaging system configured to form an image of at least a portion of an object at a focal plane;
a transporter configured to impart relative motion between the object and the focal plane so that the portion of the object that is in view of the focal plane can be varied;
at least one detector configured to receive light comprising the image of the object and provide data representing the image of the object; and
a control system configured to:
  (i) control the illumination source, the transporter, and the at least one detector during a plurality of inspection runs,
  (ii) analyze the data from the at least one detector representing the image of the object and produce data identifying a plurality of defects, and
  (iii) during at least one of the inspection runs, perform at least one post-inspection processing task on a portion of the data identifying the defects, the portion produced during an inspection run performed prior to the at least one of the inspection runs, wherein the at least one post-inspection processing task comprises calculating a defect density for a plurality of areas on the object wafer.

\* \* \* \* \*